United States Patent
O'Mahoney

[11] Patent Number: 6,142,150
[45] Date of Patent: Nov. 7, 2000

[54] COMPLIANCE COMPENSATION IN VOLUME CONTROL VENTILATOR

[75] Inventor: John O'Mahoney, Carlsbad, Calif.

[73] Assignee: Nellcor Puritan-Bennett, Pleasanton, Calif.

[21] Appl. No.: 09/047,082

[22] Filed: Mar. 24, 1998

[51] Int. Cl.[7] .................................................. A62B 19/00
[52] U.S. Cl. .............................. 128/205.18; 128/204.18; 128/204.21
[58] Field of Search ........................ 128/204.18, 204.21, 128/204.26, 205.18

[56] References Cited

U.S. PATENT DOCUMENTS

| | | | |
|---|---|---|---|
| 3,599,633 | 8/1971 | Beasley | 128/204.18 |
| 3,729,000 | 4/1919 | Bell | 128/204.18 |
| 3,820,539 | 6/1974 | Ollivier | 128/204.18 |
| 3,834,381 | 9/1974 | Peterson | 128/204.18 |
| 3,923,056 | 12/1975 | Bingmann et al. | 128/204.18 |
| 4,031,885 | 6/1977 | Davis et al. | 128/205.18 |
| 4,036,221 | 7/1977 | Hillsman et al. | 128/205.18 |
| 4,141,356 | 2/1979 | Smargiassi | 128/204.23 |
| 4,493,614 | 1/1985 | Chu et al. | 417/22 |
| 4,587,967 | 5/1986 | Chu et al. | 128/204.21 |
| 4,617,637 | 10/1986 | Chu et al. | 364/505 |
| 4,909,246 | 3/1990 | Kiske et al. | 128/205.14 |
| 4,938,212 | 7/1990 | Snook et al. | 128/205.24 |
| 4,957,107 | 9/1990 | Sipin | 128/204.21 |
| 5,044,362 | 9/1991 | Younes | 128/204.21 |
| 5,107,830 | 4/1992 | Younes | 128/204.18 |
| 5,119,810 | 6/1992 | Kiske et al. | 128/204.26 |
| 5,303,698 | 4/1994 | Tobia et al. | 128/204.21 |
| 5,531,221 | 7/1996 | Power et al. | 128/205.18 |
| 5,540,222 | 7/1996 | Younes | 128/205.18 |
| 5,546,935 | 8/1996 | Champeau | 128/205.23 |
| 5,755,223 | 5/1998 | Schaible et al. | 128/205.18 |
| 5,794,614 | 8/1998 | Gruenke et al. | 128/204.21 |
| 5,884,622 | 3/1999 | Younes | 128/204.21 |
| 5,918,597 | 7/1999 | Beasley | 128/205.18 |

*Primary Examiner*—John G. Weiss
*Assistant Examiner*—Joseph F. Weiss, Jr.
*Attorney, Agent, or Firm*—Hovey, Williams, Timmons & Collins

[57] ABSTRACT

A piston ventilator (10) includes a control circuit (80) for controlling the delivery of breathable gas to a patient circuit and thereby to the patient during patient inspiration. When operating in the volume control mode, the control circuit (80) determines the input volume of gas necessary to deliver a prescribed tidal volume to a patient while compensating for the pneumatic compliance of the ventilator (10) including the compliance of the cylinder (20) in which the piston (22) is positioned.

10 Claims, 5 Drawing Sheets

COMPLIANCE COMPENSATION IN VOLUME CONTROL VENTILATOR

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention relates to the field of piston ventilators for patients in need of respiratory assistance. More particularly, the invention is concerned with compensating for the pneumatic compliance of the ventilator including the compliance of the piston cylinder so that the prescribed tidal volume is delivered to the patient.

2. Description of the Prior Art

When a ventilator is operating in a volume control mode, a prescribed tidal volume is specified for delivery to the patient. If only the prescribed tidal volume is added to the patient circuit, the patient will receive less than this tidal volume because of the pneumatic compliance of the system. That is, as a gas volume is added, the pressure in the circuit increases and the volume delivered to the patient is less.

In order to compensate for the pneumatic compliance, prior art ventilators determine, after the completion of a breath, the shortfall in the delivered volume compared to the prescribed tidal volume. This shortfall is then added to the input volume on the next patient inspiration. However, because of pneumatic compliance, the added amount may be insufficient to ensure delivery of the prescribed volume. The shortfall is again determined and a new additional volume added during the next inspiration. As many as eight iterations over eight breaths may be required before the prescribed tidal volume is actually delivered to the patient.

The prior art problem of compensating for pneumatic compliance is more acute with piston ventilators. This is because the piston can end up in a different position within the cylinder at the end of each breath. In other words, the system compliance is not static, but rather, changes with each breath. As a result, prior art piston ventilators have been unable to provide the prescribed tidal volume with the desired level of precision and reliability.

SUMMARY OF THE INVENTION

The present invention solves the prior art problems discussed above and provides a distinct advance in the state of the art. More particularly, the piston ventilator hereof compensates for pneumatic compliance including the variable compliance of the cylinder in order to provide the prescribed tidal volume with precision and reliability.

The preferred ventilator includes a control circuit for controlling the piston motor so that the input volume delivered by the cylinder at the beginning of inspiration is sufficient to compensate for the pneumatic compliance of the ventilator in order to deliver the prescribed tidal flow to the patient. The control circuit includes a signal processor responsive to pressure signals from the cylinder and from the patient circuit to determine the needed input volume by predicting the compliance of the effective cylinder volume at the end of the next inspiration. Other preferred aspects of the present invention are disclosed herein.

DETAILED DESCRIPTION OF THE PREFERRED EMBODIMENT

Figure 1:
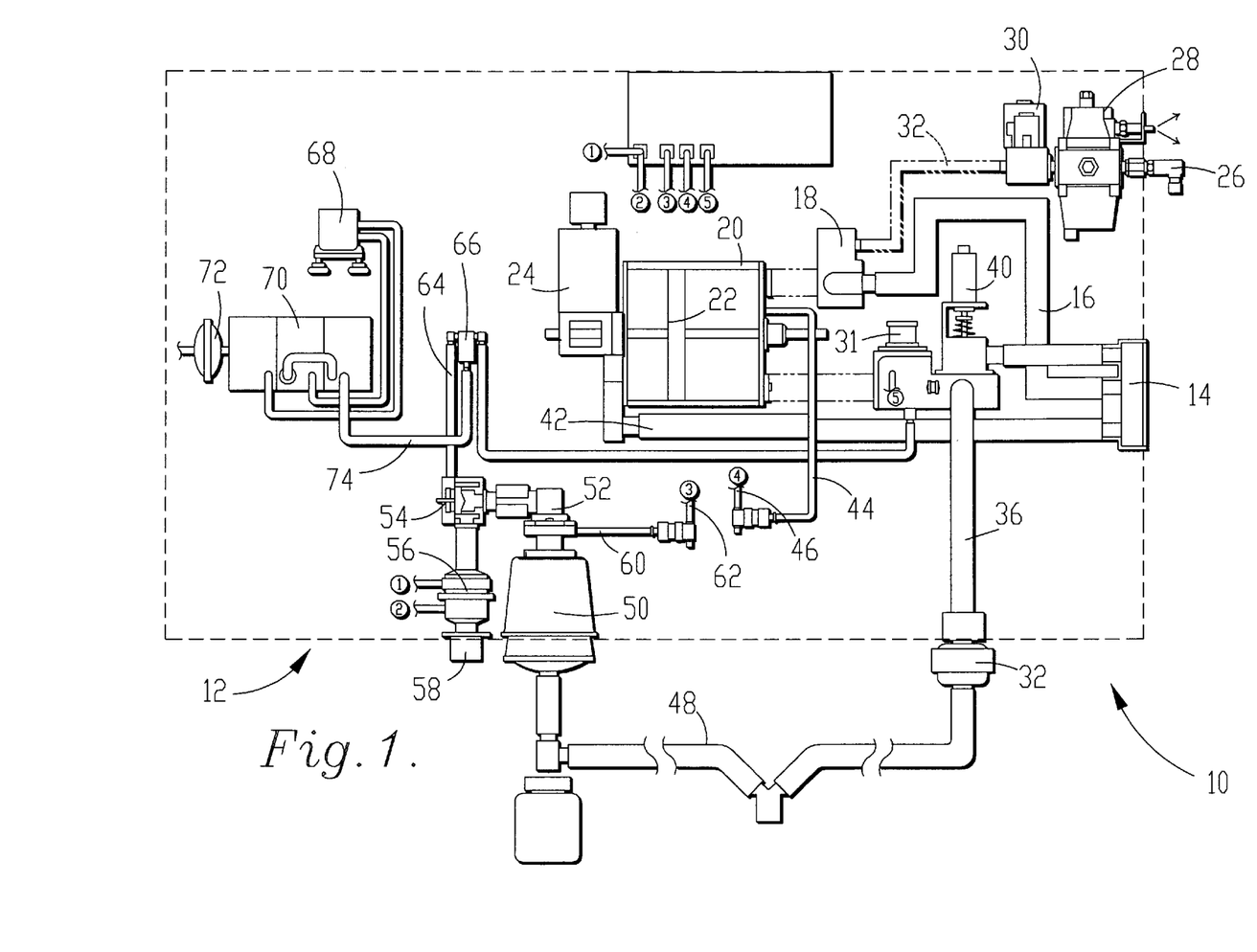
FIG. 1 is a diagram of the pneumatic system of the preferred piston ventilator in accordance with the present invention.

FIG. 1 illustrates preferred ventilator 10 in accordance with the present invention. More particularly, FIG. 1 illustrates pneumatic system 12 of the ventilator. Pneumatic system 12 broadly includes inhalation components, exhalation components, and the PEEP components.

The piston inhalation components include air intake filter 14, intake line 16 and mixing manifold 18 connected to the check valve inlet of cylinder 20 containing piston 22 driven by piston motor 24. The piston air intake components further include oxygen fitting 26, oxygen regulator 28, oxygen solenoid 30 and oxygen inlet line 32 connected with manifold 18 for mixing oxygen with ambient air received through filter 14. As such, the mixture is the gas delivered to the patient by ventilator 10. The check valve outlet of cylinder 20 is connected to oxygen sensor 31. Inhalation line 36 interconnects oxygen sensor 31 with the patient by way of the inspiratory filter 32. Safety valve 40 is connected to line 36 adjacent sensor 31. The inhalation components also include line 42 for exhausting air from cylinder 20 during retraction of piston 22. Line 44 interconnects cylinder pressure transducer 46 (Pcyl) with cylinder 20 on the discharge side of piston 22.

The exhalation components include exhalation line 48 connected with the patient thereby common with inhalation line 36. Exhalation line 48 connects to expiratory filter 50 and from there through heater assembly 52, exhalation valve 54 and exhalation flow sensor 56 to exhaust outlet 58. The exhalation components also include line 60 interconnecting exhalation pressure transducer 62 (Pexp) with expiratory filter 50. Line 64 interconnects exhalation solenoid 66 with exhalation valve 54.

The PEEP components include PEEP pump 68 connected as shown to PEEP reservoir 70, which receives inlet air through filter 72. Line 74 connects reservoir 70 with exhalation solenoid 66.

Figure 2A:
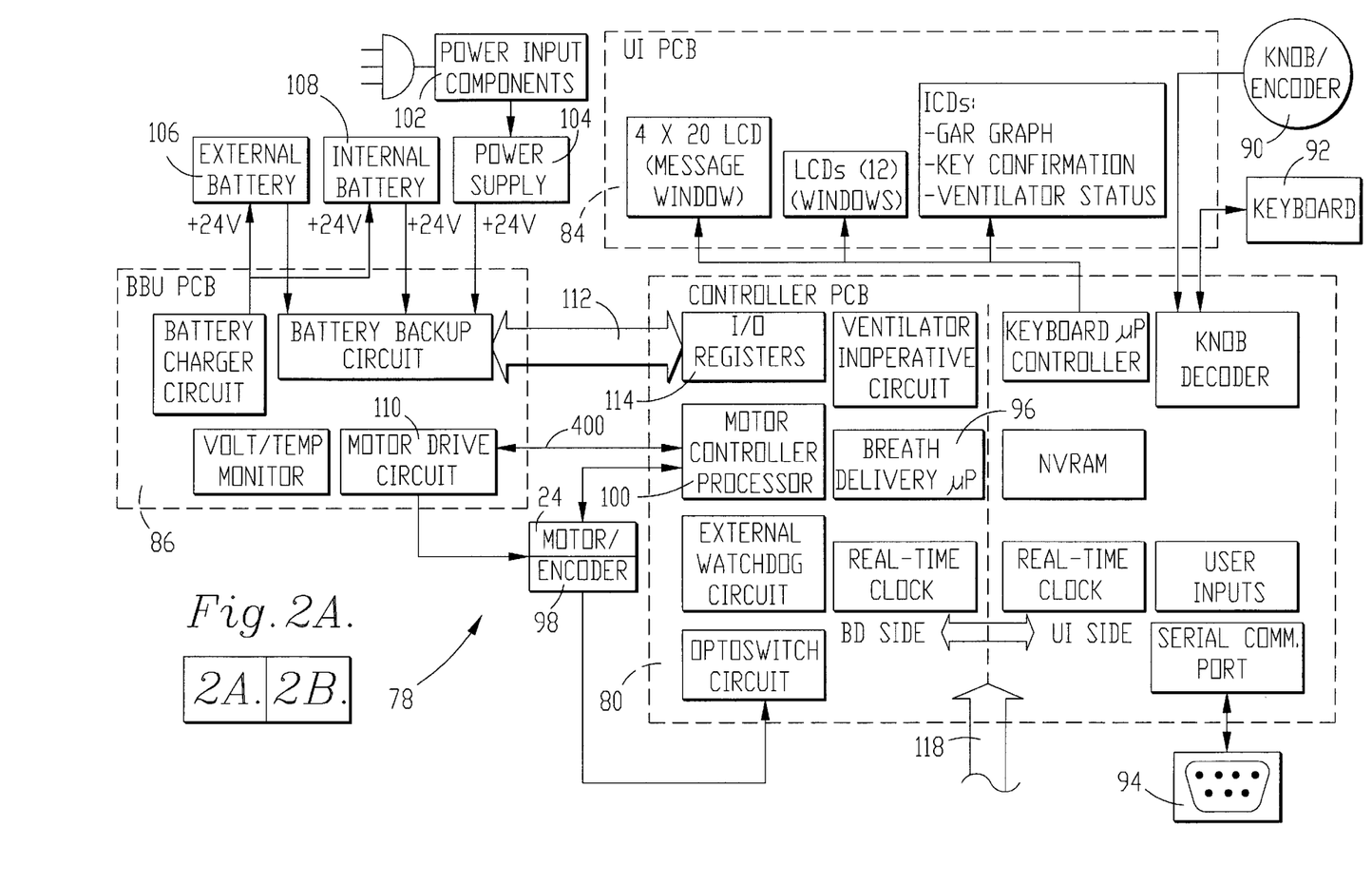
FIG. 2A is an electrical diagram illustrating a first portion of the electrical system of the ventilator of FIG. 1.
Figure 2B:
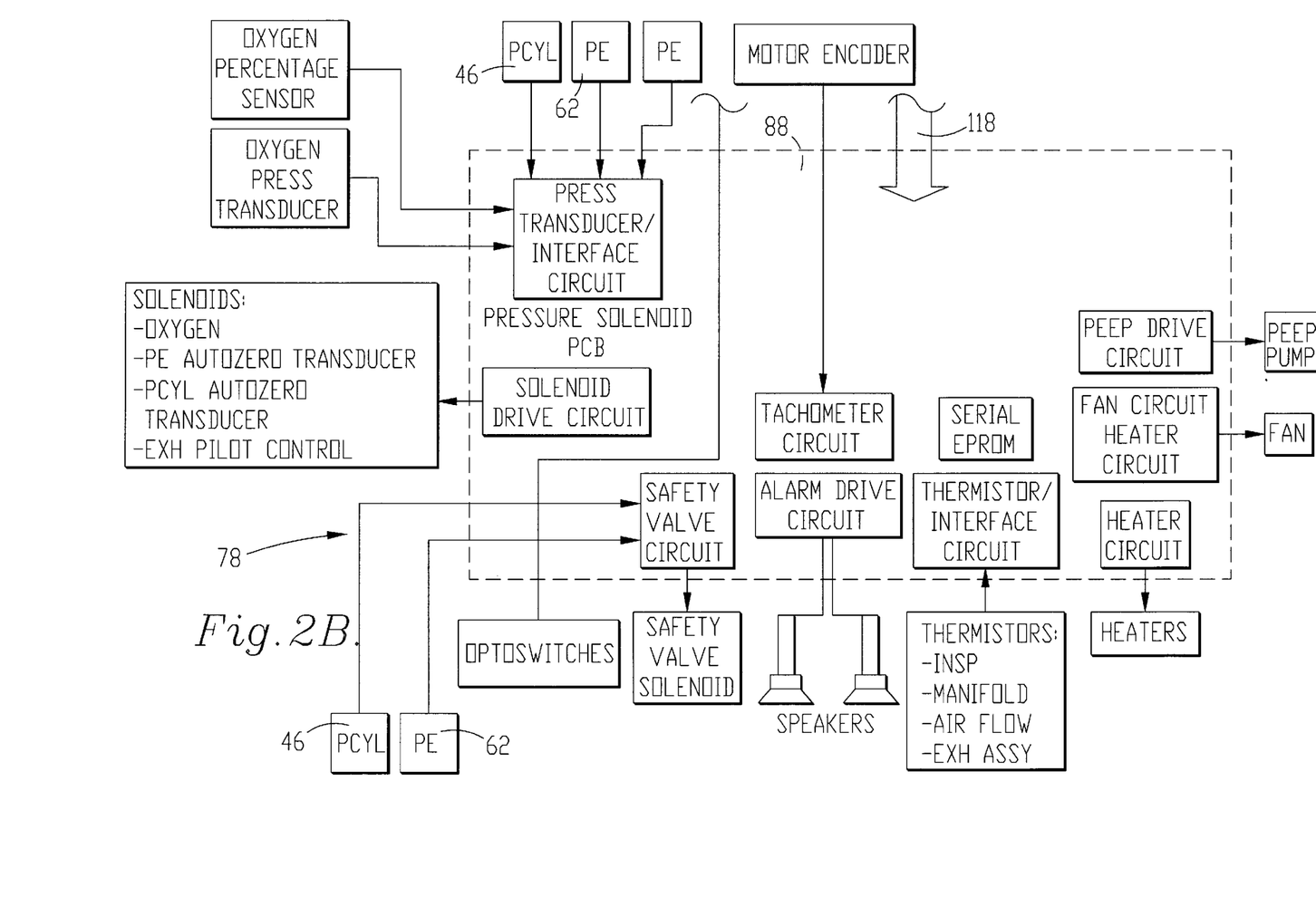
FIG. 2B is an electrical diagram illustrating the second portion of the electrical system of the ventilator of FIG. 1.

FIGS. 2A and 2B illustrate the electrical system 78 for operating ventilator 10. Electrical system 78 broadly includes main control circuit 80, display circuit 84 and motor controller 86 as illustrated in FIG. 2A, and solenoid circuit 88 illustrated in FIG. 2B.

Main control circuit 80 includes the components labeled therein and interconnects with components 82–88 as shown. In addition, main control circuit 80 receives inputs from knob encoder 90 for entering inspiration target pressure, PEEP pressure, pressure rise time during inspiration, and breath timing when in the pressure control mode. Main control circuit 80 is also connected with keyboard 92 and serial port 94.

Main control circuit 80 further includes a digital processor in the nature of breath delivery microprocessor 96 under control of a computer program stored therein. Microprocessor 96 receives inputs from motor controller microprocessor 100 representative of the position and movement of piston motor 24 by way of motor controller interface 100 and encoder 98.

Display circuit 84 receives data from main control circuit 80 for providing the various displays indicated in FIG. 2A.

Motor controller 86 receives operating power from a conventional household supply by way of power input components 102 and power supply 104. Motor controller 86 is also connected to external battery 106 and internal battery 108 that provide backup power in the event of external supply disruption. Motor drive circuit 110 connects with piston motor 24 and drives motor 24 in accordance with the motor control signals received over bus 400 from motor controller microprocessor 100 (114).

As illustrated in FIG. 2B, solenoid circuit 88 operates as the control interface for the various solenoids and transducers. Specifically, circuit 88 receives inputs from exhalation pressure transducer 62 and cylinder transducer 46. These transducers function as pressure sensors coupled with the patient circuit for indicating the pressure therein. The sensor signals representative thereof are converted to analog sensor signals in interface circuit 116. These analog sensor signals are transmitted by way of bus 118 to main control circuit 80 as input to breath delivery microprocessor 96 where the signals are converted to digital.

Figure 3:
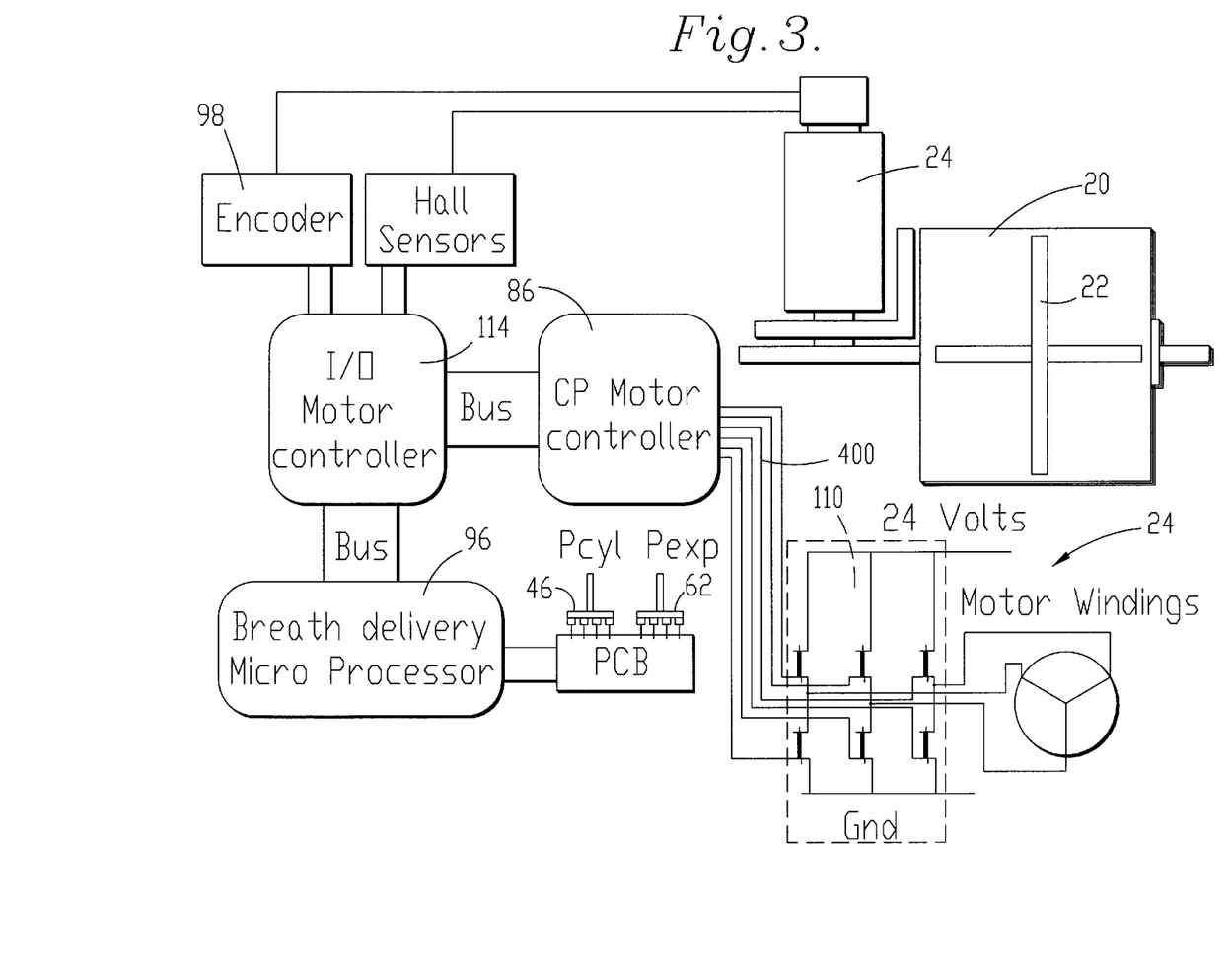
FIG. 3 is a block diagram illustrating the preferred control circuit shown coupled with the piston motor and pressure sensors of the ventilator of FIG. 1.

FIG. 3 is a simplified block diagram showing selected components from FIGS. 1, 2A and 2B used in controlling the operation of piston motor 12 and thereby piston 22 and the pressure in the patient circuit. In general, the patient circuit includes those pneumatic passages of ventilator 10 in communication with the patient.

In operation, breath delivery microprocessor 96 as the preferred digital processor receives sensor signals from cylinder pressure transducer (Pcyl) 46 and exhaust pressure transducer (Pexp) 62. In response, microprocessor 96 provides motor control signals to motor controller 86 by way of I/O register 114. In response to the motor control signals, motor controller activates piston motor 24 and the windings thereof in order to drive piston 22 for delivering gas to the patient circuit at a gas pressure and flow. Motor encoder 98 provides motor position signals to microprocessor 96 by way of I/O register 114.

Figure 4:
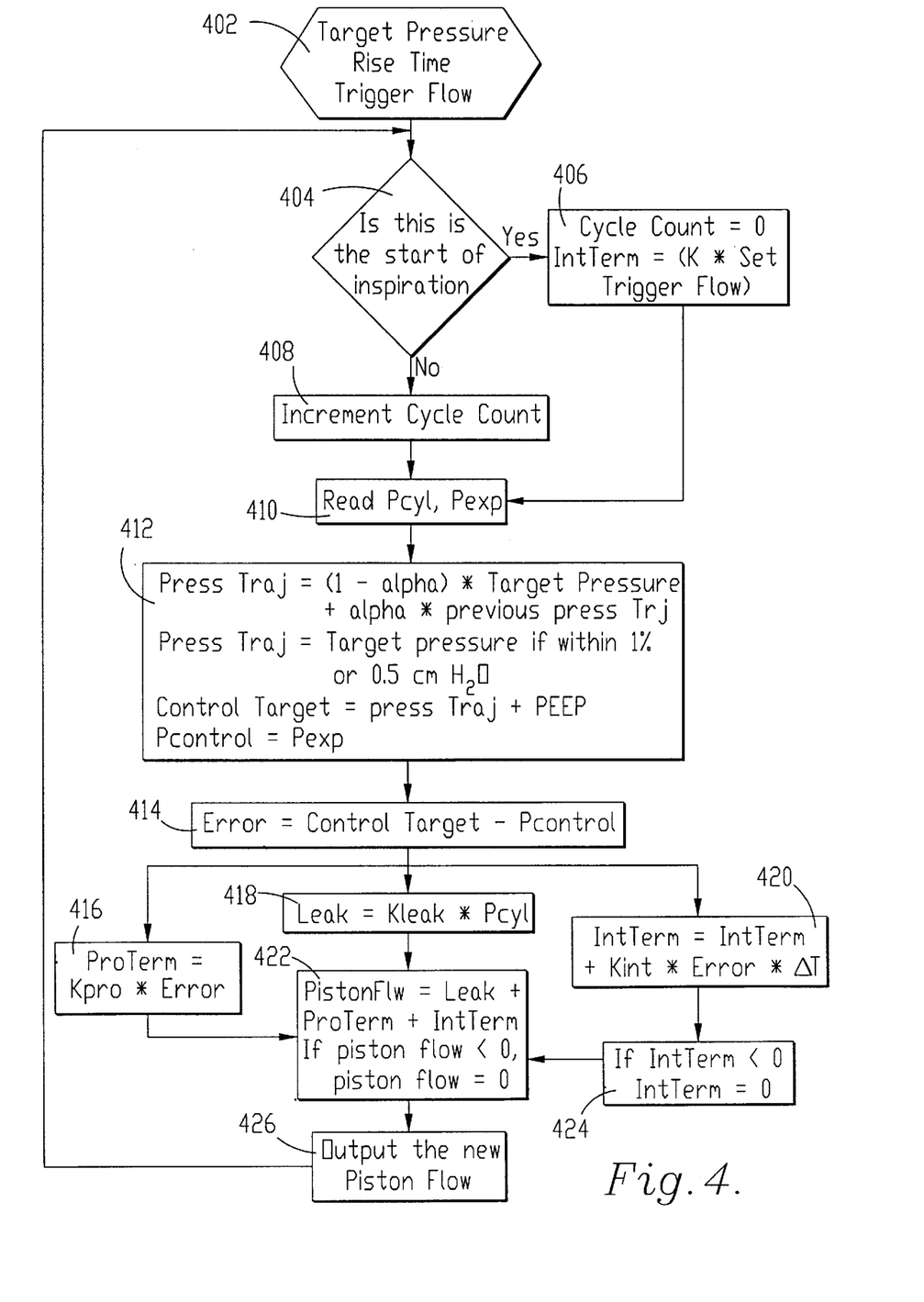
FIG. 4 is a flow chart illustrating the preferred computer program for operating the control circuit of FIG. 3.

FIG. 4 is a flow chart of pertinent portions of the preferred computer program for controlling the operation of microprocessor 96 in order to control the operation of piston motor 24. FIG. 4 illustrates operation in the pressure control ventilation mode where the initiation of a breath is on a timed basis. The present invention is also useful in the pressure support mode in which the onset of patient inspiration may trigger ventilator 10 to provide pressurized gas in the patient circuit to assist inspiration.

The program illustrated in FIG. 4 enters at step 402 and retrieves initialization data from the nonvolatile random access memory (NVRAM) illustrated in FIG. 2A. This initialization data includes the target pressure during patient inspiration, the rise time for the increase in the pressure in the patient circuit during patient inspiration, and the trigger flow which is the flow in the patient circuit indicating the onset of patient inspiration.

Pressure Control

Step 404 then asks whether this pass through the program loop indicates the start of patient inspiration. If yes, step 406 sets the variable "cycle count" to zero, and sets the variable "integration term" (IntTerm) as equal to a constant K times the current trigger flow minus the set trigger flow.

If the answer in step 404 is no, indicating that this is not the first pass through the program loop, step 408 increments the cycle count variable. Next, step 410 reads the current pressure indicated by the sensor signals provided by transducers 46 and 62 as the variables Pcyl and Pexp.

Step 412 calculates the variable Press Traj which is the current pressure on a pressure trajectory or curve for the rise of the pressure during inspiration. As indicated, the variable Press Traj is a function of the constant alpha which is derived from the desired rise time for the gas pressure in the patient circuit. In particular, $$\text{alpha}=\exp(-1/\text{tau}-\Delta T)$$

wherein, $$\text{tau}=\text{rise time (in seconds)}/3$$

where the rise time is between 0 and 95% of target. This yields a value for alpha as 0.501 rounded to 0.5. A higher value for tau yields a smaller value for alpha which results in a more rapid rise from the beginning pressure to the target pressure.

For example, if alpha is 0.5 and the target pressure is 10 cm water, then the first term in the equation for Press Traj is (1−0.5)×10 cm which equals 5 cm. The second term is zero because this is the first calculation for Press Traj. Accordingly, the initial set point pressure is 5 cm.

During the next pass through the program loop, the second term will be 2.5 cm (0.5×5 cm) and the new Press Traj will be 7.5 cm (5 cm+2.5 cm). On the third calculation, Press Traj will be 8.75 cm and, on the fourth, will be 9.375 cm, and so forth. Thus, each value of Press Traj is one of a plurality of points on the pressure trajectory or curve that reflects the desired rise time for the inspiration pressure.

As will be appreciated, the value of Press Traj approaches the target pressure in the limit. However, if Press Traj is within 1% or with 0.5 cm water of the target pressure, whichever is greater, then Press Traj is set equal to the target pressure.

Step 412 next determines the control target, or current set point pressure, as the value of Press Traj plus the PEEP pressure. That is, the PEEP pressure is already present in the patient circuit at the beginning of inspiration. The target pressure is the increase in pressure delivered to the patient circuit. Finally, step 412 sets the variable Pcontrol equal to Pexp, which is the current pressure in the patient circuit as measured by transducer 62.

Step 414 calculates the error as the difference between actual pressure (Pcontrol) in the patient circuit and the current set point pressure (Control Target). After the error is calculated, the task is to change the air flow in the patient circuit by the amount necessary to correct the error so that the gas pressure in the patient circuit substantially conforms to the set point pressure. To accomplish this, steps 416, 418, and 420 calculate the individual correction terms to be used in step 422.

Step 416 calculates the proportional term (ProTerm) as the error times a proportional constant (Kpro). The constant Kpro is empirically derived for ventilator 10 as being high enough to provide substantial correction without adding instability to the system.

Step 418 calculates the leak term for compensating for leakage in the system. The system leakage is substantially the amount of leakage between piston 22 and cylinder 20. The clearances between piston 22 and cylinder 20 are designed to reduce friction. In so doing, a certain amount of leakage is expected, and the leakage is proportional according to the constant Kleak to the pressure (Pcyl) in cylinder 20 as indicated by transducer 46.

Step 420 calculates an integration term (IntTerm) as the previous IntTerm plus an integration constant (Kint) times the error over time ($\Delta T$). The initial integration term is set in step 406 as discussed above. This term integrates the error over time so that the error can be eliminated. That is, if only proportional correction is used, the error is never specifically eliminated and can accumulate over time. The integration term corrects this problem. The time frame for $\Delta T$ is 10 ms, which is the sampling time used in the preferred embodiment.

Step 422 determines the gas flow amount (PistonFlw) as provided by piston 22 to the patient circuit necessary to correct the error according to the correction terms calculated in steps 416–420. Specifically, the variable PistonFlw is the sum of the three correction terms.

It will be noted, however, that in step 424, the integration term is set equal to zero if determined as less than zero in step 420. This can happen if the error is negative, that is, if the actual pressure is above the set point. In such cases, setting the integration term to zero precludes a calculation that the piston should reverse direction. Any overshoot is rapidly eliminated by the leakage around the piston.

Finally, step 426 provides motor control signals to motor controller 86. These motor controller signals represent the new gas flow amount to be produced by piston 22 for correcting the error. In other words, the motor control signals are representative of the gas flow amount necessary from piston 22 so that the actual gas pressure as measured by transducer 62 conforms substantially to the current set point (Control Target). Motor controller 86 responds to the motor controller signals from breath delivery microprocessor 96 (by way of I/O register 114) by operating motor 24 at the speed necessary so that piston 22 produces the needed gas flow amount for correcting the error. Encoder 98 provides confirmation of the current motor speed and thereby the current gas flow amount.

The program then loops from step 426 back to step 404. During the second and subsequent passes through the program loop, the answer in step 404 is no, and step 408 increments the cycle count variable. The program then repeats steps 410–426 for the balance of patient inspiration.

Compliance Compensation in Volume Control Mode

The preferred computer program is also operable to control the operation of microprocessor 96 in order to control the operation of piston motor 24 in the volume control mode. In this mode, the delivery of the input volume by the cylinder assembly (including cylinder 20, piston 22 and piston motor 24) to the patient circuit can be triggered by patient inspiration or on a timed basis.

Immediately prior to each patient inspiration, the program determines the input volume according to the input volume formula:

$$Vi = Vt[1+((Ct+Vc-Vi-Vl) \div Pa)) \div Cl]$$

where
Vi is the input volume,
Vt is the prescribed tidal volume,
Ct is the compliance of the tubing or patient circuit,
Vc is the current cylinder volume,
Vi is the previous input volume,
Vl is the volume lost to leakage,
Pa is atmospheric pressure, and
Cl is the effective lung compliance, which is calculated as discussed below.

This formula is calculated iteratively before each inspiration until Vi is within 2 mL of the previous Vi. In an example, the following values are used for the respective variables listed above starting with Vt: 500 mL, 2 mL/cm water, 1000 mL, 500 mL (this is Vi for the first iteration), 100 mL 1032 cm water, and 20 mL/cm water. Vi is 559.69 after the first iteration, 558.244 after the second iteration and 558.279 after the third. Volumes are expressed in terms of the standard for body temperature and pressure saturated (BTPS).

After the fourth iteration, Vi is 558.278 and no further iterations are performed. That is, motor control signals are delivered to motor 24 in order to activate delivery of 558.279 mL as the input volume by the cylinder assembly to the patient circuit. With this input volume, the prescribed tidal volume of 500 mL will be delivered to the patient on the next inspiration with the difference (58.278) being the additional volume necessary to compensate for the compliance of the system and for leakage.

As will be appreciated, these iterations of the formula are performed before delivering the input volume. As a result, the patient is provided with a prescribed tidal flow upon the first or second breath.

From the input volume formula, one will note the term Vc-Vi. This term predicts the effective cylinder volume, which is the volume between the piston and the cylinder outlet. The piston is controlled so that it retracts to begin another stroke when the effective cylinder volume is about 750 mL. A prescribed tidal volume does not exceed this volume. Accordingly, by subtracting Vi (the input volume) from Vc (the current effective volume of the cylinder), the effective volume of the cylinder is predicted at the end of the next inspiration.

In the example, Vc is 1000 mL and Vi is 558.278 mL with the difference being 441.722 mL, which is the predicted effective volume of the cylinder after delivering Vi as the input volume to the patient circuit. Ignoring volume lost to leakage (Vl), the predicted cylinder compliance is 0.428, which is the predicted effective cylinder volume (441.722) divided by Pa (1032 cm water).

The cylinder assembly must also deliver sufficient volume to compensate for the volume lost to leakage (Vl) and this value is also subtracted from the current cylinder volume before determining the cylinder compliance. In the example, Vl is 100 mL. Thus, the predicted cylinder compliance, (Vc-Vi-Vl)/Pa, is 0.3311 mL/cm water.

By predicting the effective volume of the cylinder at the end of the next inspiration, the effective compliance of the cylinder can also be predicted. With this information, it can be determined in advance how much input volume is needed to ensure that the prescribed tidal volume is delivered to the patient.

The program also determines the volume lost to leakage (Vl) for use in the input formula as $$Vl = \Sigma Kl * Pcyl * Vis * T$$

where
Kl is a calibrated leak constant of the piston cylinder leak rate in terms of STPD conditions, Pcyl is the pressure in the cylinder, Vis is a factor for viscosity compensation for temperature and gas composition, and T is the sample period which is 10 ms. That is, a leak amount is determined for each 10 ms sample period, and the leak amounts summed for all of the sample periods during the inspiratory time to determine the total volume lost to leakage. The inspiratory time is the tidal volume divided by the peak flow expressed in the BTPS standard. In the preferred embodiment, the flow delivery is a square wave but the invention is equally applicable to other forms including descending ramp and sinusoidal.

For the input volume formula, the program also calculates the term Cl which is the effective lung compliance as $$Cl=(Vi-Vt-Vc)/(PexpEnd-PexpStart)$$

where PexpEnd is the expiratory pressure at the end of inspiration and PexpStart is the pressure at the beginning of inspiration. Also, $$Vt=((PiEnd+PexpEnd)-(PiStart+PexpStart))*0.5*Ct$$

where Pi is the pressure in the patient circuit adjacent the outlet of the cylinder. The factor 0.5 takes the average of Pi and Pexp at the beginning and end of inspiration to compensate for pressure losses in the pressure circuit. Ct is the compliance in the patient circuit or tube.

Finally, $$Vc=(PcylEnd-PcylStart)*Ccyl$$

where Ccyl is the compliance of the predicted effective cylinder volume at the end of the next inspiration. In the preferred embodiment, the program uses a running average of Cl over three breaths.

It will be appreciated that the utility of the program for the input volume formula is not limited to piston ventilators with a calibrated leak constant. For example, in a piston ventilator without leakage, the term Vl is zero. Moreover, the program can be used with non-piston ventilators such as proportional solenoid ventilators. In such cases, the term Vc also becomes zero and the input volume formula reduces to $$Vi=Vt[1+Ct/Cl].$$

Those skilled in the art will appreciate that the present invention encompasses many variations in the preferred embodiment described herein. Having thus described this embodiment, the following is claimed as new and desired to be secured by Letters Patent:

What is claimed is:

1. A ventilator comprising:
   a cylinder assembly comprising a cylinder having an outlet and a shiftable piston therein to deliver gas to the outlet;
   a patient circuit coupled with the cylinder outlet for conveying cylinder-derived gas to a patient during gas-supplemented inhalations;
   a PEEP assembly operatively coupled with said cylinder assembly for maintaining a constant pressure within said patient circuit during patient exhalation,
   said cylinder having varying piston starting positions and effective compliances at the beginning of said gas-supplemented inhalations; and
   a control circuit operatively coupled with said cylinder assembly and including;
      a cylinder pressure sensor coupled with said cylinder for sensing the gas pressure therein and providing cylinder pressure signals representative thereof;
      a patient circuit pressure sensor coupled with said patient circuit for sensing gas pressure therein and providing patient circuit pressure signals representative thereof;
      a signal processor coupled with said sensors and operable for receiving said pressure signals therefrom, said signal processor operable to determine, using said received pressure signals, a predicted compliance of said cylinder at the end of a gas-supplemented inhalation and a compliance-compensated volume of gas to be delivered by said cylinder assembly for said gas-supplemented inhalation, and to generate an output representative of said compliance-compensated volume of gas; and
      a controller coupled with said signal processor and cylinder assembly in order to receive said output and operate said cylinder assembly to deliver said compliance-compensated volume of gas, so that the patient receives a desired tidal volume of gas from the cylinder assembly notwithstanding the position of said piston within said cylinder and the compliance of said cylinder at the beginning of said inhalation.

2. The ventilator of claim 1, said signal processor operable to determine said compliance-compensated volume of gas immediately prior to said gas-supplemented inhalation.

3. The ventilator of claim 1, said signal processor operable to determine the leakage loss of gas from said cylinder during operation of said cylinder assembly, and to generate an output representative of a compliance and leakage loss-compensated volume of gas to be delivered to said patient, said controller operating said cylinder assembly to deliver said compliance and leakage loss-compensated volume of gas.

4. The ventilator of claim 1, said signal processor operable to determine said compliance and leakage loss-compensated volume of gas calculated using the formula $$Vi=Vt\ [1+((Ct+(Vc-Vi_{prev}-Vl)\div Pa))\div Cl]$$

where Vi is said compliance and leakage loss-compensated volume, Vt is said tidal volume, Ct is the compliance of said patient circuit, Vc is the volume of said cylinder at the time of said determination, $Vi_{prev}$ is a previously determined compliance and leakage-loss compensated volume, Vl is the volume of said leakage loss, Pa is atmospheric pressure and Cl is the effective lung compliance of the patient.

5. A method of operating a piston ventilator to deliver volumes of gas during respective gas-supplemented patient inhalations, said ventilator including a cylinder assembly comprising a cylinder having an outlet and a shiftable piston therein to deliver gas to the outlet, a patient circuit coupled with the cylinder outlet for conveying cylinder-derived gas to said patient during said gas-supplemented inhalations, and a PEEP assembly operatively coupled with said cylinder assembly for maintaining a constant pressure within said patient circuit, said cylinder having vary piston starting positions and compliances at the beginning of said gas-supplemented inhalations, said method comprising the steps of:
   determining a compliance-compensated volume of gas to be delivered by said cylinder assembly for a gas-supplemented patient inhalation so that the patient receives a desired tidal volume of gas from the cylinder assembly notwithstanding the position of said piston within said cylinder and the compliance of the cylinder at the beginning of said inhalation,
   said determining step comprising the steps of sensing the gas pressure conditions within said cylinder and patient circuit, and generating respective cylinder and patient circuit pressure signals representative of said pressure conditions;

using said respective pressure signals to predict the compliance of said cylinder at the end of said gas-supplemented inhalation, and to determine said compliance-compensated volume of gas to be delivered for said inhalation; and operating said cylinder assembly to deliver said determined compliance-compensated volume of gas through said patient circuit to said patient.

6. The method of claim 5, including the step of determining said compliance-compensated volume of gas immediately prior to said gas-supplemented inhalation.

7. The method of claim 5, said determining step being carried out in a signal processor.

8. The method of claim 5, including the step of determining the leakage loss of gas from said cylinder during operation of said cylinder assembly, and operating said cylinder assembly to deliver a compliance and leakage loss-compensated volume of gas through said patient circuit to said patient.

9. The method of claim 8, wherein said compliance and leakage loss-compensated volume of gas is calculated using the formula $$Vi = Vt\ [1+((Ct+(Vc-Vi_{prev}-Vl)\div Pa))\div Cl]$$

where Vi is said compliance and leakage loss-compensated volume, Vt is said tidal volume, Ct is the compliance of said patient circuit, Vc is the volume of said cylinder at the time of said determination, $Vi_{prev}$ is a previously determined compliance and leakage-loss compensated volume, Vl is the volume of said leakage loss, Pa is atmospheric pressure and Cl is the effective lung compliance of the patient.

10. The method of claim 9, said formula calculation being carried out iteratively until the values of Vi of successive calculations are within 2 mL of each other.

* * * * *